(12) United States Patent
Backes

(10) Patent No.: US 10,207,680 B2
(45) Date of Patent: Feb. 19, 2019

(54) LENS PLATE

(71) Applicant: TRW AUTOMOTIVE ELECTRONICS AND COMPONENTS GMBH, Radolfzell (DE)

(72) Inventor: Ulrich Backes, Radolfzell (DE)

(73) Assignee: TRW AUTOMOTIVE ELECTRONICS & COMPONENTS GmbH (DE)

( * ) Notice: Subject to any disclaimer, the term of this patent is extended or adjusted under 35 U.S.C. 154(b) by 123 days.

(21) Appl. No.: 15/124,829

(22) PCT Filed: Mar. 17, 2015

(86) PCT No.: PCT/EP2015/055581
§ 371 (c)(1),
(2) Date: Sep. 9, 2016

(87) PCT Pub. No.: WO2015/140181
PCT Pub. Date: Sep. 24, 2015

(65) Prior Publication Data
US 2017/0182978 A1  Jun. 29, 2017

(30) Foreign Application Priority Data
Mar. 20, 2014 (DE) ........................ 10 2014 103 849

(51) Int. Cl.
| | |
|---|---|
| *B60S 1/08* | (2006.01) |
| *G02B 3/00* | (2006.01) |
| *G02B 27/09* | (2006.01) |
| *G02B 19/00* | (2006.01) |

(Continued)

(52) U.S. Cl.
CPC ............ *B60S 1/0837* (2013.01); *G02B 3/005* (2013.01); *G02B 19/0014* (2013.01); *G02B 19/0085* (2013.01); *G02B 27/0927* (2013.01); *G02B 27/0955* (2013.01); *B60S 1/0833* (2013.01); *G01N 21/552* (2013.01); *G02B 3/08* (2013.01)

(58) Field of Classification Search
CPC ... B60S 1/0837; G02B 27/0955; G02B 3/005; G02B 3/08; G01N 21/552
See application file for complete search history.

(56) References Cited

U.S. PATENT DOCUMENTS

| | | |
|---|---|---|
| 5,811,793 A | 9/1998 | Pientka |
| 5,838,454 A | 11/1998 | Pientka |
| 5,839,823 A | 11/1998 | Hou et al. |

(Continued)

FOREIGN PATENT DOCUMENTS

| | | |
|---|---|---|
| CN | 2758759 | 2/2006 |
| CN | 203037879 | 7/2013 |

(Continued)

*Primary Examiner* — Tony Ko
(74) *Attorney, Agent, or Firm* — Tarolli, Sundheim, Covell & Tummino LLP

(57) ABSTRACT

In a lens plate (18) for an optical sensor device in a vehicle, in particular for a rain sensor, with a transmitter-side lens structure (26) and a receiver-side lens structure (32), the transmitter-side lens structure (26) partially is provided with anti-transmission features which in individual regions of the lens plate (18) partially or completely prevent the passage of the light emitted by a light transmitter (14).

11 Claims, 3 Drawing Sheets

(51) Int. Cl.
 *G02B 3/08* (2006.01)
 *G01N 21/552* (2014.01)

(56) References Cited

U.S. PATENT DOCUMENTS

| | | |
|---|---|---|
| 5,898,183 A | 4/1999 | Teder |
| 8,269,202 B2 | 9/2012 | Backes |
| 2002/0094495 A1* | 7/2002 | Ono .................. G02B 3/08 430/321 |
| 2008/0297803 A1 | 12/2008 | Backes |
| 2009/0261237 A1 | 10/2009 | Backes |
| 2011/0164329 A1* | 7/2011 | Jiang .................. G02B 3/08 359/742 |
| 2013/0240739 A1* | 9/2013 | Shpater ............. G08B 29/046 250/353 |

FOREIGN PATENT DOCUMENTS

| | | |
|---|---|---|
| DE | 3806881 | 9/1989 |
| JP | 2011027491 | 2/2011 |
| WO | 2009015988 | 2/2009 |
| WO | 2009024597 | 2/2009 |
| WO | 2009112096 | 9/2009 |

* cited by examiner

LENS PLATE

RELATED APPLICATIONS

This application corresponds to PCT/EP2015/055581, filed Mar. 17, 2015, which claims the benefit of German Application No. 10 2014 103 849.5, filed Mar. 20, 2014, the subject matter, of which are incorporated herein by reference in their entirety.

BACKGROUND OF THE INVENTION

This invention relates to a lens plate for an optical sensor device in a vehicle, in particular for a rain sensor, with a transmitter-side lens structure and a receiver-side lens structure.

Rain sensors in vehicles, which detect the wetting of a pane, include a light transmitter, a lens plate attached to the pane with a coupling layer, and a light receiver. The lens plate includes a transmitter-side and a receiver-side lens structure, which each consist of a light input and a light output structure.

The light emitted by the light transmitter is coupled into the lens plate by means of the transmitter-side light input structure and converted to substantially parallel light beams which vertically traverse the lens plate. The transmitter-side light output structure deflects the light bundle by about 45°, so that after traversing the coupling layer and the glass it reaches the outer surface thereof. There, the light bundle is totally reflected and again traverses glass and coupling layer. The receiver-side light input structure again directs the light bundle vertically through the lens plats, before it is focused onto the surface of the light receiver by the receiver-side light output structure.

During wetting of the surface of the pane, a part of the light is coupled out at the surface of the pane. Thus, only a part of the light is reflected. By means of the variation of the intensity of the reflected light which is reflected back onto the light receiver, the wetting of the pane thus can be detected.

In the lens plates known from the prior art, the light distribution on the windshield, however, is not uniform, but has a distinct peak in the middle and a strong decrease towards the edge. Wetting in the edge region, in which the light intensity is distinctly lower, thus leads to a lower loss of light than wetting in the middle of the measurement region. Wetting in the edge region thus is hard to detect due to the small light difference. The surface which can be utilized for defecting the wetting of the pane thus is substantially smaller than the actually illuminated surface.

SUMMARY OF THE INVENTION

It is the object of the invention to provide a lens plate with which a larger surface or a larger region of the pane can be utilized for detecting wetting.

For the solution of the object there is provided a lens plate for an optical sensor device in a vehicle, in particular for a rain sensor, with a transmitter-side lens structure and a receiver-side lens structure, wherein the transmitter-side lens structure partially is provided with anti-transmission features which in individual regions of the lens plate partially or completely prevent the passage of the light emitted by a light transmitter.

The invention is based on the consideration of changing the transmitter-side lens structure such that the light intensity at the pane is reduced in the usually light-intensive regions, in particular in the middle of the illuminated surface, whereas in the less light-intensive regions the light intensity is not influenced. Ideally, the light intensity in the light-intensive regions is attenuated such that a substantially homogeneous illumination of the entire illuminated region of the pane is achieved.

The attenuation of the light is achieved in that the passage of the light through the lens plate is partially or completely prevented in individual regions, so that in this region no light or only an attenuated light can exit from the lens plate in direction of the pane. The regions are formed and positioned such that the measurement region on the pane is illuminated more uniformly, so that a larger surface can be utilized for detecting wetting.

When the passage of light through the lens plate is reduced by these regions, this attenuation for example is chosen such that the light impinging on the pane approximately has the same intensity as in the regions in which the passage of light is not reduced by anti-transmission features.

Even if the passage of light is completely impeded in individual regions by corresponding structures, a uniform light intensity can be obtained on the pane due to scattering effects behind the lens plate. In such an embodiment, the opaque regions can have a relatively small expansion and be arranged in a defined raster, so that a uniform illumination of the pane is obtained due to scattering effects.

Through the lens plate, there is deliberately sent light which is used for measuring the wetting on the pane in a measurement region on the pane. Hence, this is not parasitic light which should be prevented from coupling into the lens structure.

The anti-transmission features interact with the light sent through the lens plate. The light sent through the lens plate is at least partially attenuated by the anti-transmission features. Due to the attenuation of the light a homogeneous light distribution is obtained in the measurement region on the pane.

The area on the pane illuminated by the light thereby can completely be utilized for the measurement.

To achieve this effect, it is sufficient to apply anti-transmission features on the transmitter-side lens structure. An extension of such features to the light receiver-side region is not expedient, as in this region an attenuation of the light no longer is required.

The anti-transmission features for example can be formed by a light-scattering structure. Such structure scatters the light instead of directionally coupling the light into the lens plate or out of the same in various directions. Merely a part of the light impinging on the transmitter-side lens structure thus directly traverses the lens plane and then impinges on the pane. The number, the distance and the location or the shape of the light-scattering structures can be chosen such that a rather homogeneous light distribution is achieved on the surface of the pane.

Alternatively, the structures also can be formed flat, so that the impinging light is reflected completely and is not coupled into the lens plate or out of the same.

The anti-transmission features also can be formed by a partial coating of the lens. This coating either can reflect, absorb or attenuate the impinging light. Such coating is much easier to apply than light-scattering structures. The manufacture of the lens plate thus can be simplified distinctly. By means of the properties of the coating, for example the transparency, the positioning or the expansion of the coated regions on the lens plate, the intensity of the light entering into the lens plate or exiting therefrom in these regions can be adjusted. For this purpose, the coating for example can be completely opaque, translucent or reflecting.

To provide for an easy manufacture of the lens plate, it is also possible that the coating is printed onto the lens plate.

Usually, the lens structures of such lens plate are arranged circularly, in particular formed by a Fresnel structure. Such structure has a very strong light intensity in the middle region, which decreases towards the edge. In such a structure, the anti-transmission features preferably are provided in a radially inner region of the lens structure, whereas a radially outer region is free of the same, so that in the radially outer region the light is unimpededly coupled into the lens plate or out of the same, whereas in the radially inner region an attenuation of the light intensity is effected.

The transmitter-side lens structure for example can be formed of a Fresnel structure on a light entry side and on a light exit side. These Fresnel structures provide for an ideal coupling into or out of the lens plate with a very small overall height of the lens plate.

In such an embodiment, the anti-transmission structures can be formed by individual grooves of a Fresnel lens or a Fresnel prism, which guide the light away from the scanning region of the sensor or attenuate, block or scatter the passage of light.

These grooves of the Fresnel structure for example can have a cross-section differing from adjacent grooves, so that the same have different reflection properties or different properties of coupling in or out.

The grooves are formed such that from the entire light reflected or scattered a uniform light intensity is obtained at the pane, individual grooves also can scatter the light completely, so that it does not impinge on the pane. In addition, the scattered light bundles of individual grooves, which impinge on the pane, can be superimposed such that a uniform illumination of the pane is obtained.

Alternatively, it is also possible that these grooves are at least partly filled by a coating by which an attenuation, reflection or scattering of the light is effected.

Preferably, the anti-transmission features are provided in a radially inner region of the transmitter-side lens structure and designed such that the light intensity totally reflected at the pane largely is homogeneous, based on the measurement at the light receiver.

Independent of the embodiment of the transmitter-side lens structure, the receiver-side lens structure preferably is formed of Fresnel structures on the light entry side and on the light exit side.

BRIEF DESCRIPTION OF THE DRAWINGS

Further advantages and features can be taken from the following description in conjunction with the attached drawings, in which.

DESCRIPTION

Figure 1:
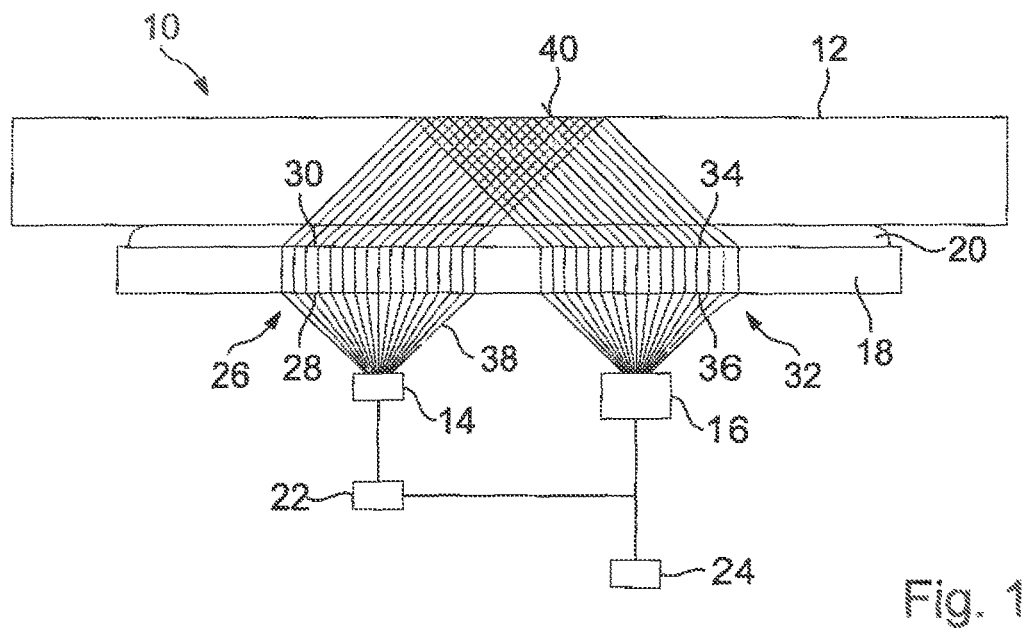
FIG. 1 shows a schematic representation of the general operating principle of a rain sensor with a lens plate.

FIG. 1 shows a schematic structure of a rain sensor 10 for detecting the wetting of a pane 12 of a vehicle. The rain sensor 10 includes a light transmitter 14, a light receiver 16 and a lens plate 18 which is mounted on the pane 12 with a coupling layer 20, in particular of silicone.

At the light transmitter 14 a controller 22 furthermore is provided, which can regulate the intensity of the light transmitter 14, as well as a signal processing unit 24 which can process the signals of the light receiver 16 and is coupled with the controller 22 of the light transmitter 14.

The lens plate 18 includes a transmitter-side lens structure 28 which consists of a first light input structure 28 facing the light transmitter 14 and a first light output structure 30 facing the pane 12. Furthermore, a receiver-side lens structure 32 is provided, which consists of a second light input structure 34 facing the pane 12 and a second light output structure 38 facing the light receiver 16.

As can be seen in FIG. 1, a light bundle 38 emitted by the light transmitter 14 is coupled into the lens plate 18 via the light transmitter-side first light input structure 28 and is converted to substantially parallel light. This light traverses the lens plate 18 and is deflected by about 45° by the light transmitter-side first light output structure 30. Subsequently, the light bundle traverses the coupler layer 20 and the pane 12, before it is reflected on the outside 40 of the pane 12.

Subsequently, the light bundle 38 traverses the pane 12 as well as the coupler layer 20 and impinges on the lens plate 18 at the receiver-side second light input structure 34. The light bundle traverses the lens plate 18 substantially vertically and is focused onto the relatively small surface of the light receiver 16 by the second light output structure 36.

By means of the controller 22 the light transmitter is controlled such that at the outlet of the light receiver 16 a specified value is achieved.

During wetting of the outside 40 of the pane 12, a part of the light bundle 38 is coupled out on the outside 40 of the pane 12. As a result, only a part of the light bundle 38 is reflected, so that a decrease of the output signal can be detected at the light receiver 16. When a certain threshold value is exceeded, the wetting of the pane 12 is regarded as detected.

Figure 2:
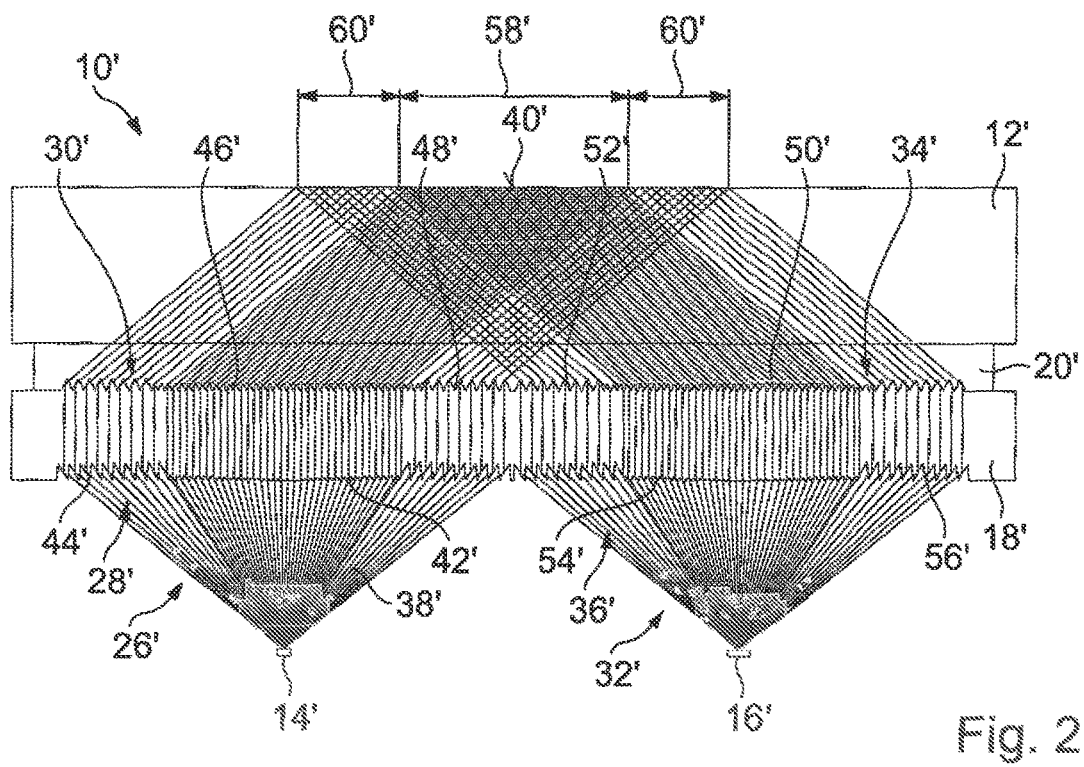
FIG. 2 shows a sectional view of a rain sensor with a lens plate according to the prior art.

FIG. 2 shows a rain sensor 10' from the prior art. The light input structures 28', 34' as well as the light output structures 30', 36' each consist of Fresnel lenses, by which a corresponding deflection of the light bundle is possible with a very small overall height of the lens plate 18'.

As can be seen in FIG. 2, the light input structures 23', 34' as well as the light output structures 30', 36' each consist on an inner region 42', 46', 50', 54' and an outer region 44', 48', 52', 56'. The same each are formed such that the impinging light is coupled into the lens plate, traverses the lens plate 18' vertically to its direction of extension, and impinges on the pane 12' at an angle of about 45°, subsequently is reflected at the pane 12' and is focused on the light receiver 16' by the receiver-side lens structure 32'.

As can furthermore be seen in FIG. 2, the light intensity of the light bundle, which exits from the middle region 46' of the first light output structure 30', is higher than in the outer region 48'. On the one hand, this is due to the construction of the Fresnel lenses. In the outer region 48' of the light output structure 30', there also is a partial shading of the individual prism structures by adjacent structures due to the flatter incidence angle of the light.

Figure 4:
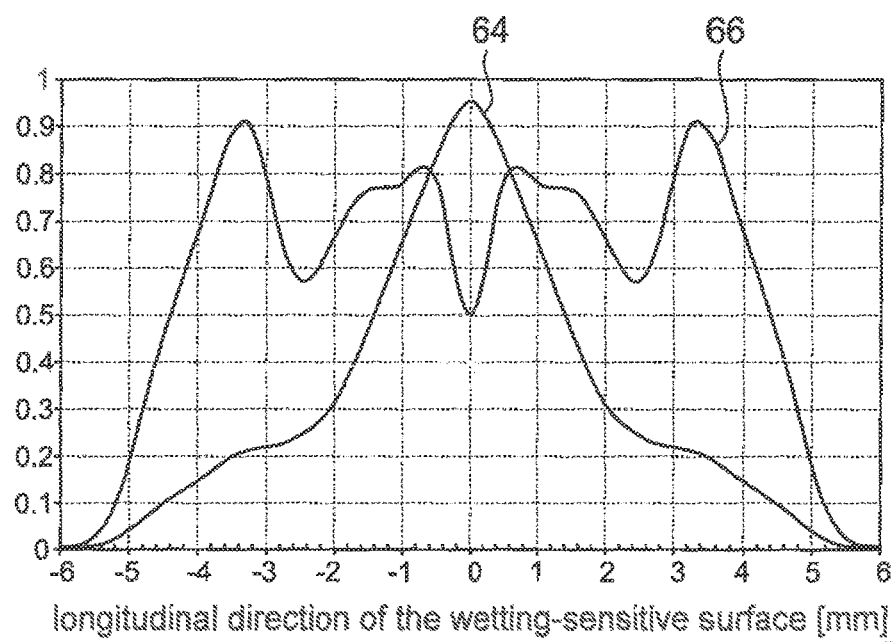
FIG. 4 shows a representation of the light distribution of the rain sensors of FIGS. 2 and 3.

In a middle region 58' of the pane 12', the light intensity therefore is distinctly higher than in the edge regions 60'. A distribution of the light intensify relative to the distance to the center of the illuminated outside 40' is represented in FIG. 4 with the reference numeral 64. This leads to the fact that a wetting of the inner region 58' leads to a much stronger decrease of the light intensity than in an outer edge region 60'. Thus, wetting in the edge regions 60' possibly cannot be detected or only in the case of stronger wetting, as the decrease of the light intensity is too low. An increase of the light intensity, however, also would lead to an increase of the light intensity in the middle region 58', so that an output of light in the edge regions 60' can again not be detected.

Figure 3:
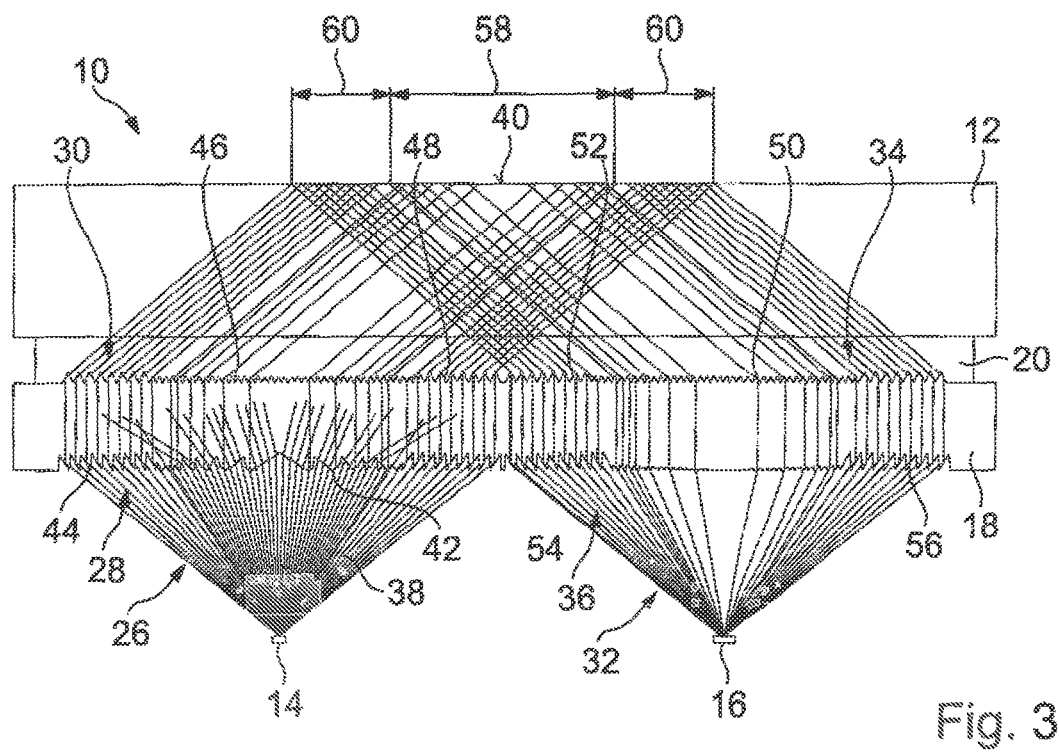
FIG. 3 shows a sectional view of a rain sensor with a lens plate according to the invention.

To solve this problem and to produce a uniform light intensity on the entire illuminated outside 40 of the pane 12, a lens plate 18 according to the invention is used in the rain sensor 10 shown in FIG. 3. The lens plate 18 substantially corresponds to the lens plate 18' shown in FIG. 2. The lens plate 18 merely differs in that the inner region 42 of the first light input structure 28 includes anti-transmission features, in this case light-scattering structures 62.

As can be seen in FIG. 3, the light impinging on these structures 82 is not coupled into the lens plate 18 in parallel or vertically, but is scattered in the lens plate 18. As a result, distinctly less light exits from the inner region 46 of the transmitter-side first light output structure 30. The light intensity in the inner region 58 of the pane 12 thus is reduced distinctly, whereas the light in the outer regions 44, 48 can unimpededly pass through the lens plate 18 and impinge on the edge regions 60.

The light distribution of the assemblies 10 shown in FIGS. 2 and 3 relative to the distance to the center of the illuminated outside 40 is shown in FIG. 4 by way of comparison. FIG. 4 shows the light intensity measured at the light receiver relative to the longitudinal direction of the wetting-sensitive outside 40, which is shown e.g. in FIG. 3. A first curve 64 represents the light distribution of the rain sensor 10' of FIG. 2, a second line 66 the distribution of the rain sensor 10 with the lens plate 18 according to the invention as shown in FIG. 3.

As can clearly be seen, the rain sensor 10' with the lens plate 18 of the prior art has a very high light intensity in the inner region 58, which strongly decreases towards the edge regions 60.

The line 66 on the other hand shows that with the lens plate 18 according to the invention a more homogeneous light intensity can be produced over a very wide range of −3 to +3 mm, in that the light intensity is attenuated in the inner region 58. A decrease of the light intensity in the inner region 58 below the value of the outer edge region 60 represents no problem, since the outer edge region 60 has a distinctly larger surface area, so that in this case, too, a much larger surface is present for detecting the wetting of the pane 12. Ideally, however, the light intensity at the pane 12 substantially has an equally high value on the entire surface.

Although no light passes through the lens plate 13 in individual regions due to a print, a coating or a corresponding formation of the structures, a homogeneous illumination nevertheless is achieved due to the slight beam expansion as a result of the imperfect workmanship of the Fresnel lenses during manufacture, in that the gaps produced by fading out are again partly filled up. In addition, the light bundles which are scattered at individual structures can be superimposed such that a uniform light intensity is achieved at the pane 12.

Thus, the invention generally aims at designing individual regions of the first lens structure 26 such that in the inner region 42 less light or no light at all can pass through the lens plate 18 and impinge on the pane 12.

Figure 5:
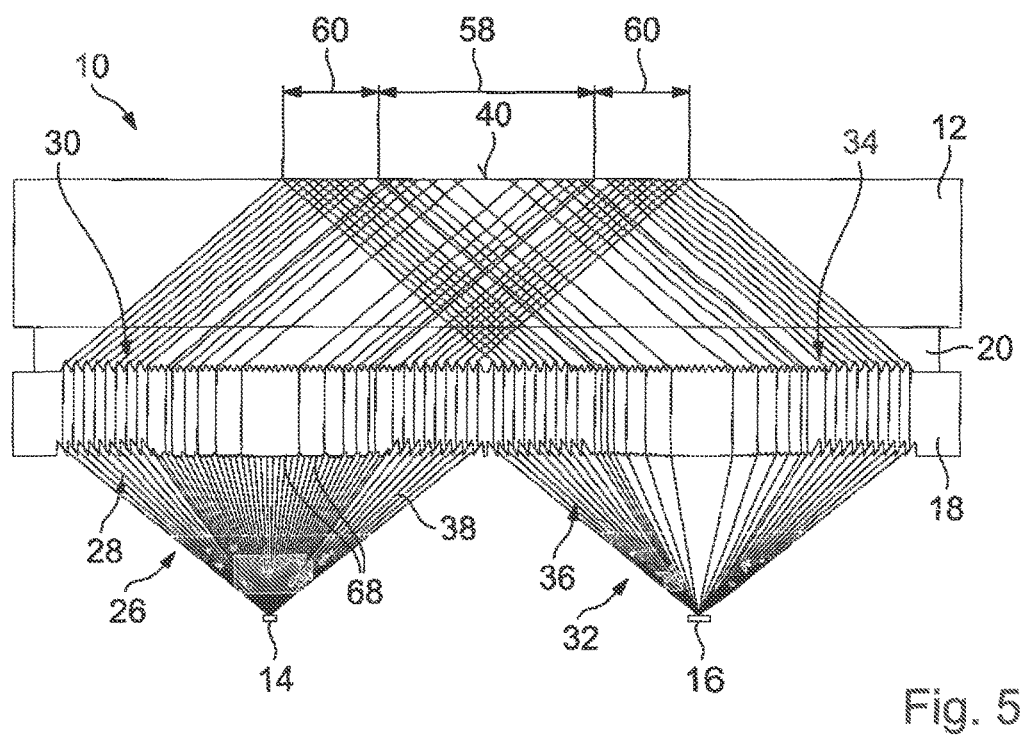
FIG. 5 shows a sectional view of a rain sensor with a second embodiment of lens plate according to the invention.

As can be seen in FIG. 3, this can be effected by more light-refracting structures 62. Alternatively, as is shown for example in FIG. 5, this can also be effected by printing individual regions 63 of the surface of the lens plate 18. These regions 68 can be flattened, as can be seen in FIG. 5.

It is, however, also possible that the first light input structure 26 is a conventional Fresnel structure and merely individual grooves are printed. The print can be reflecting, translucent or light-absorbing.

It is also possible to partially coat the lens plate, wherein the coating likewise can be of the reflecting, partly transparent or light-absorbing type.

In the embodiments shown here, the anti-transmission features each are provided on the first light input structure 28. It is, however, also possible to provide the same on the first light output structure 30, i.e on the pane side at the lens plate 18.

Fading out in any case is effected onto the light transmitter-side lens structure 26. An arrangement of such anti-transmission features on the light receiver-side lens structure would lead to the fact that light beams coming from outside the glass, for example from the sun or from approaching vehicles, might be directed onto the light receiver 16. Consequently, this might lead to wrong detections.

The invention claimed is:

1. A lens plate (18) for an optical sensor device in a vehicle, in particular for a rain sensor, with a transmitter-side lens structure (26) and a receiver-side lens structure (32), wherein the transmitter-side lens structure (26) partially is provided with anti-transmission features which in individual regions of the lens plate (18) partially or completely prevent the passage of the light emitted by a light transmitter (14), wherein light sent through the lens plate is at least partially attenuated by the anti-transmission features such that a homogeneous light distribution is obtained in an entire illuminated region of a pane.

2. The lens plate according to claim 1, wherein the anti-transmission features are formed by a light-scattering structure.

3. The lens plate according to claim 1, wherein the anti-transmission features are formed by a partial coating of the lens plate (18).

4. The lens plate according to claim 3, wherein the coating is printed.

5. The lens plate according to claim 1, wherein the anti-transmission features are provided in a radially inner region (42, 46) of the lens structure (26), whereas a radially outer region (44, 46) is free of the same.

6. The lens plate according to claim 1, wherein the transmitter-side lens structure (28) is formed of Fresnel structures on a light entry side and on a light exit side.

7. The lens plate according to claim 6, wherein the anti-transmission structures can be formed by individual grooves of a Fresnel lens or a Fresnel prism, which guide the light away from the scanning region of the sensor or attenuate or block the passage of light.

8. The lens plate according to claim 6, wherein the grooves have a cross-section differing from adjacent grooves.

9. The lens plate according to claim 6, wherein the grooves are at least partly filled by a coating.

10. The lens plate according claim 1, wherein the anti-transmission features are provided in a radially inner region (42, 46) of the transmitter-side lens structure and designed such that the light intensity totally reflected at the pane (12) largely is homogeneous, based on the measurement at the light receiver.

11. The lens plate according to claim 1, wherein the receiver-side lens structure (32) is formed of Fresnel structures on the light entry side and on the light exit side.

* * * * *